(12) United States Patent
Muz et al.

(10) Patent No.: US 6,606,512 B2
(45) Date of Patent: Aug. 12, 2003

(54) ARRANGEMENT FOR THE FIXING OF A MEDICAL-TECHNICAL MEASURING DEVICE AS WELL AS A MEDICAL-TECHNICAL MEASURING DEVICE INVOLVING THIS SORT OF ARRANGEMENT, PARTICULARLY A PULSOXIMETER SENSOR

(75) Inventors: Edwin Muz, Reutlingen (DE); Christof Muz, Reutlingen (DE)

(73) Assignee: Nicolay Verwaltungs-GmbH, Nagold (DE)

( * ) Notice: Subject to any disclaimer, the term of this patent is extended or adjusted under 35 U.S.C. 154(b) by 21 days.

(21) Appl. No.: 09/884,422

(22) Filed: Jun. 20, 2001

(65) Prior Publication Data

US 2002/0016537 A1 Feb. 7, 2002

(30) Foreign Application Priority Data

Jun. 23, 2000 (DE) .......................... 100 30 862

(51) Int. Cl.⁷ .................................. A61B 5/00
(52) U.S. Cl. ...................... 600/344; 600/322
(58) Field of Search ................. 600/322, 323, 600/340, 344, 499; 602/9, 20–22, 46, 48, 61–64, 901; 606/201–203; 623/57, 65; 250/221, 239

(56) References Cited

U.S. PATENT DOCUMENTS

| 4,685,464 | A | | 8/1987 | Goldberger et al. |
| 5,638,818 | A | * | 6/1997 | Diab et al. ................ 600/479 |
| 5,766,131 | A | | 6/1998 | Kondo et al. |
| 5,807,266 | A | * | 9/1998 | Itonaga et al. ............ 600/479 |
| 5,891,026 | A | * | 4/1999 | Wang et al. ............... 600/344 |
| 5,919,133 | A | * | 7/1999 | Taylor et al. ............. 600/344 |

FOREIGN PATENT DOCUMENTS

DE       3703458      8/1991

\* cited by examiner

*Primary Examiner*—Eric F. Winakur
*Assistant Examiner*—David J. McCrosky
(74) *Attorney, Agent, or Firm*—Roylance, Abrams, Berdo & Goodman, LLP.

(57) ABSTRACT

An arrangement for fixing a medical-technical sensor, particularly a pulsoximeter sensor, to a patient's body part includes a carrier for supporting a sensor and a longitudinal opening for receiving the body part. The carrier includes a foam material part elastically deformable for the fixing. The deformation provides a force-accumulation arrangement. The medical-technical sensor for measuring physiological data can be combined with such arrangement. The sensor includes optical electronic measuring parts arranged on the carrier.

20 Claims, 2 Drawing Sheets

ARRANGEMENT FOR THE FIXING OF A MEDICAL-TECHNICAL MEASURING DEVICE AS WELL AS A MEDICAL-TECHNICAL MEASURING DEVICE INVOLVING THIS SORT OF ARRANGEMENT, PARTICULARLY A PULSOXIMETER SENSOR

FIELD OF THE INVENTION

The present invention relates to an arrangement for fixing a medical-technical measuring device to a patient's body part, and to medical-technical measuring device having such fixing arrangement, particularly a pulsoximeter sensor.

BACKGROUND OF THE INVENTION

DE 37 03 458 C2 discloses a medical-technical measuring device including arrangement fixing it a body part of a patient, particularly to a finger, a toe, an arm or a leg. A first segment of a carrier means includes a longitudinal opening extending in a longitudinal direction to receive the body part, and supports the measuring means. A second segment, adjacent the first segment, extends around the periphery and is elastic. During stressing beyond the material elasticity of the first segment, the stresses pass to the second segment. The disclosed method of manufacture involves casting around the transmitter and receiver elements, during the manufacture of the carrier means.

U.S. Pat. No. 4,685,464 discloses a clothespin-like pulsoximeter. Two arms of a clamp-like carrier means can be brought into clamping contact on the body part of the patient.

The conventional fixing arrangements and measuring devices are disadvantageous in that they include a secure fixing obtained by introduction of a higher force level and essentially pointed or clamping fixing forces, which then, for example, can lead to disturbances of the blood circulation in the body part, or in that they guarantee good blood circulation in the body part by use of reduced fixing forces, which then frequently lead to the fixing arrangement or the measuring device becoming detached from the body part, particularly upon displacement of the body part. This latter arrangement can be an important disadvantage, particularly when it is used for infants or small children and for intensive care medicine. Also, the conventional devices are costly to manufacture and require a high degree of precision and high level of skill with their use.

SUMMARY OF THE INVENTION

The present invention involves an arrangement for fixing a medical-technical measuring device to the body as well as a medical-technical measuring device, which overcome the disadvantages of conventional arrangements and devices. Particularly, the present invention ensures a secure fixing, while preventing any disturbances of the blood circulation of the body part of the patient. In addition, the fixing arrangement and measuring device can be manufactured at low cost, and are to be simple to use and to clean.

In pulsoximetry, the oxygen content of the blood of a patient is determined. Preferably, a body part with good blood circulation is exposed to rays or even irradiated with light, for example, of two different wave lengths. The relative oxygen saturation of the blood is calculated from the absorption and/or reflection. Suitable body parts for this type of measuring are, for example, the ear and the nose separating wall, but particularly the extremities such as the fingers or toes. For such medical-technical measuring device, at least one optical transmitter element and at least one optical receiver element are preferably arranged on opposite sides of the body part. On the one hand, the blood circulation of the body part is not to be obstructed. On the other hand, the elements are to be sufficiently secured in their position relative to one another, particularly in their axial alignment, so that the measuring process is not at all negatively influenced even with frequent movements of the body part, for example in the case of infants and/or of intensive care patients.

The arrangement for fixing a medical-technical measuring device according to the present invention has carrier means including a foam part. At least on the surface of the carrier means turned toward or facing the body part, the carrier means is slightly elastically deformable to obtain the fixing. The deformation makes available a force-accumulating arrangement which brings about the fixing, so that a secure fixing is attained with essentially unimpaired blood circulation of the body part. Preferably, the foam of the carrier means completely surrounds the body part, conducting the fixing force over the entire surface of the body part, and particularly is configured as a sheathing or in cap-like configuration. The exterior surface of the carrier means and the interior surface formed by the longitudinal opening can be configured as cylindrical, conical or frustoconical. With the introduction of the body part into the longitudinal opening or the slipping of the carrier means over the body part, deformation of the foam occurs particularly in radial direction in relation to the longitudinal direction. The foam material thus has the advantageous property that it can be pressed together on one fragment of its volume, and thus, makes available a permanent force-accumulation arrangement.

The term "foam material" is not intended to mean the original material forming the foam, but rather is intended to mean the solid foam product itself, in other words the synthetically produced material of cellular structure. Among other things, rubber, a rubber-plastic mixture and particularly a synthetic resin or plastic can be considered as the raw material to make the foam material. Some synthetic foam materials, which can be used, are cited in Neumuller, Otto-Albrecht: Rompp Chemie-Lexikon, Stuttgart, Francksche Verlagsanstalt [Publisher], 8th Edition, page 3703, under the key word "Schaumkunststoffe" ["Synthetic foam"]. Because of the low density of the foam material, both the device for the fixing and also the medical-technical measuring device are of low mass. The longitudinal opening can be a blind hole or a through-passage opening and can be arranged in the center or eccentrically in relation to the longitudinal axis of the carrier means. Preferably, in any case, the axis of the longitudinal opening extends parallel to the axis of the carrier means. The diameter of the longitudinal opening is preferably somewhat smaller than the diameter of the smallest body part to which the measuring device is to be affixed.

The foam material or the entire carrier means can be manufactured of a semifinished material by stamping or cutting, particularly with use of a water stream or a laser beam. Thus, both the density and the cell dimensions of the foam material, as well as the material of the foam itself, can be adapted optimally to the relevant particular use being proposed. Generally speaking, such manufactured foam material parts or carrier means have neither blind holes nor any structures deviating from a cylindrical shape.

With the foam material part having incisions originating from the longitudinal opening and extending at least some distance in the longitudinal direction, at least two segments are formed by the incisions around the periphery, and extend in peripheral direction. Potential tensile stresses generate a deformation such that disturbing the measuring method is prevented. The number of incisions and the number of segments formed by the incisions can be adapted to the dimensions and configuration of the body part.

The incisions extend radially through at least half of the thickness of the foam part. An appreciable compensation for the deformation of one segment is then guaranteed by the deformation of an adjacent segment. Thus a permanently reliable and tight contact of the foam material on the body part is guaranteed.

The segments are connected with one another on their exterior by a layer of foam material configured of one single piece with the segments. The exterior shape of the carrier means during introduction of the body part or while the arrangement is being slipped over a body part is then not varied noticeably. Optimum contact of the foam material on the body part is guaranteed on all sides. For example, in the case of a measuring device with optical electronic measuring means, when the body part is displaced or turned over, the light is reliably prevented from getting to the receiver either directly from the transmitter or through reflection. This feature can be attained either alternatively or as a supplement by the foam material being colored with a dye. The dye is adapted to an optical electronic measurement to be carried out by the measuring device. Particularly, the radiation originating from a transmitter element is essentially completely absorbed.

The permanently secure fixing is further improved by the shape of the longitudinal opening being designed to be the shape of the body part which will receive it. For example, the longitudinal opening to receive a finger or a toe can be configured in conical shape with at least two padding pieces or beads. The padding pieces or beads are arranged one behind the other in the direction of the longitudinal layout, separated from one another by a narrowed section and rounded either inward or outward.

The carrier means has a transverse opening into which the measuring means is to be inserted, particularly on opposite sides of the body part. A secure and, if necessary, detachable mounting of the measuring means and an exact axial alignment of one to the other are then guaranteed. By such detachable mounting of the measuring means, the carrier means can be exchanged simply and at low cost if it becomes necessary, for instance for hygienic requirements.

A connection to the measuring means can be attached to a point on the exterior of the carrier means. The arrangement for fixing to a body part and the associated measuring device are then simple to manage and operate. Furthermore, fatiguing bending stresses of the connecting line and the connection points are particularly avoided, whereupon the operation and maintenance costs of the measuring device are also lowered considerably. The mounting can be executed by catch devices configured, for example, of one piece and mounted on the exterior.

On its exterior side more distant from the body part, the carrier means can have a rigid casing around the foam material. The stability of the exterior shape of the carrier means as well as a sufficient level of fixing force are then guaranteed. The casing, for example, can be formed by a sheathing of plastic or metal. Alternatively or as a supplement, an integral or structural foam material with solid skin and cellular core, all of one piece can be formed. The exchangeability of the foam material is further simplified when the sheathing is of a plurality of parts, particularly when it can be opened for the introduction of the foam material. For example, the sheathing can have an articulation-like device so that it can be opened, which device is configured preferably of one or more of the sheathing parts integrated into one piece.

The present invention also relates to a medical-technical measuring device for measuring physiological data of a patient, particularly a pulsoximeter sensor, with a fixing arrangement as described above. The measuring device has optical electronic measuring means arranged on the carrier means. A measuring procedure yielding reliable physiological data is then guaranteed by using a measuring device configured according to the present invention. In addition, the measuring device according to the present invention is of low cost to manufacture and maintain, as well as being simple to use.

The measuring means can include at least one optical transmitter element and at least one optical receiver element. The elements are arranged along the same axis through a transverse opening on opposite sides of the carrier means. The axial alignment of transmitter and receiver elements is guaranteed even under the mechanical stress of the arrangement for the fixing, for example, during introduction of the body part or during slipping of the arrangement over the body part. The foam material of the carrier means is essentially impermeable for the radiation emitted from the optical electronic measuring means. Particularly, it can be tinted with a corresponding suitable dye. In this manner, erroneous measurements, occurring for example because of reflections of the emitted radiation on the foam material, are essentially excluded from occurring.

Other objects, advantages and salient features of the present invention will become apparent form the following detailed description, which, taken in conjunction with the annexed drawings, discloses preferred embodiments of the present invention.

BRIEF DESCRIPTION OF THE DRAWINGS

Referring to the drawings which form a part of this disclosure.

DETAILED DESCRIPTION OF THE INVENTION

Figure 1:
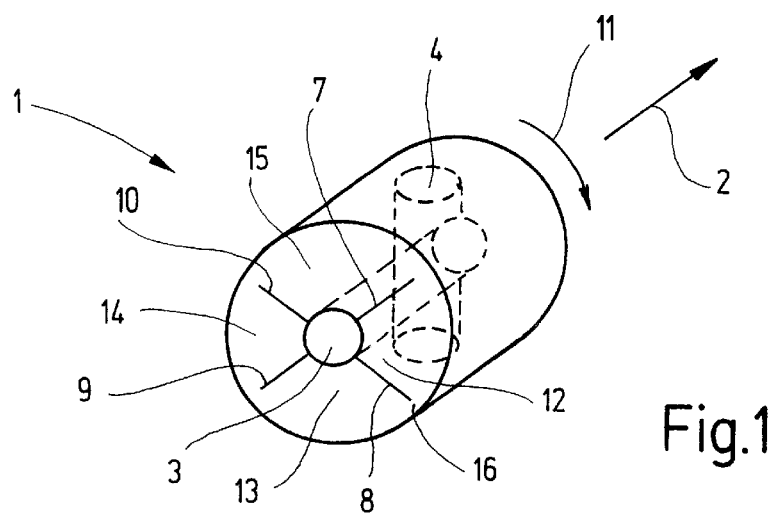
FIG. 1 is a perspective view of a foam material part of a carrier according to a first embodiment of the present invention.

FIG. 1 shows a perspective view of a foam material part 1 of a carrier or carrier means of a device according to the present invention for fixing of medical-technical measuring device, particularly a pulsoximeter sensor, to a body part of a patient. The foam material part 1 has a longitudinal opening 3 extending in a longitudinal direction 2 to receive the body part. Furthermore, foam material part 1 has a transverse opening 4 extending in a straight line and essentially at a right angle to longitudinal direction 2, into which the measuring means 5 and 6 is inserted.

Foam material part 1 consists of a foam material which can be slightly elastically deformed during the introduction of the body part into longitudinal opening 3 and/or during the slipping of the measuring device over the body part. The deformation makes available a force-accumulating arrangement which brings about the fixing.

In the embodiment shown in FIG. 1, foam part 1, longitudinal opening 3 and transverse opening 4 are of circular cylindrical configurations. Longitudinal opening 3 extends from a frontal end of foam part 1 as far as the opposite, reverse end. Transverse opening 4 extends from a point on the covering surface near the border of foam part 1 to the diametrically opposite point on the cover surface, and thus, intersects longitudinal opening 3. The diameter of longitudinal opening 3 is somewhat smaller than the smallest body part to be received therein. The diameter of transverse opening 4 is adapted to the measuring means 5 and 6 to be inserted therein.

Foam material part 1 has four incisions or slits 7, 8, 9 and 10 originating from longitudinal opening 3 and extending at least for some distance in longitudinal direction 2, forming four segments 12, 13, 14 and 15 around the periphery 11. Incisions 7, 8, 9 and 10 extend in radial direction through at least half the thickness of foam part 1, preferably as far as a few millimeters below or within the exterior surface. The four segments are connected with one another around their exterior by a layer 16 formed of one integral piece with segments 12, 13, 14 and 15 and passing all the way around the foam material part. In the embodiment of FIG. 1, incisions 7, 8, 9 and 10 extend along the entire axial length of foam material part 1, are radially aligned in a straight line and form four identical segments 12, 13, 14, 15 with regard to their dimensions and particularly their angle extensions. In this embodiment longitudinal opening 3 is arranged in the center of cylindrical foam material part 1.

Figure 2:
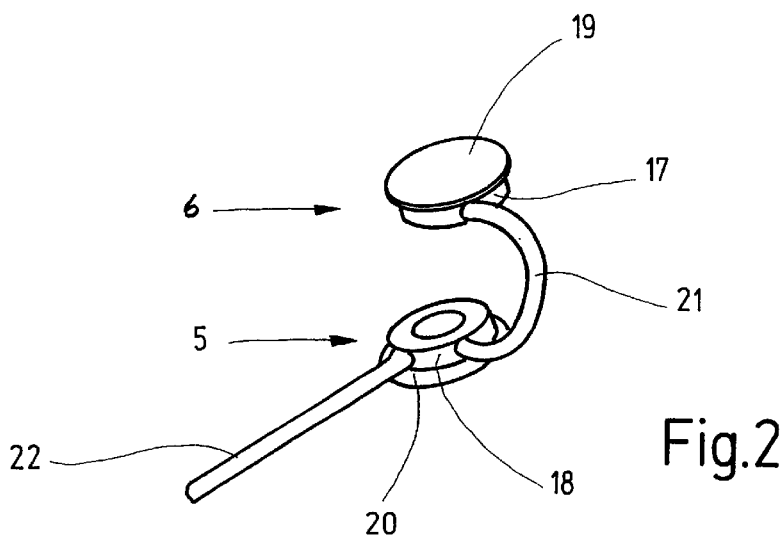
FIG. 2 is a perspective view of the optical electronic measuring means of a medical-technical measuring device according to the present invention.

FIG. 2 shows the optical electronic measuring means or sensor 5 and 6 of a medical-technical measuring device of the present invention, particularly a pulsoximeter sensor. The device includes at least one optical transmitter element 6 and at least one optical receiver element 5, which can be inserted into the ends of transverse opening 4 of foam part 1, which ends are opposite one another. For this purpose, transmitter element 6 and receiver element 5 have plug segments 17 and 18, respectively. The plug segments are cylindrical in this embodiment, but if necessary can be conical in shape, and guarantee proper guiding during insertion into foam part 1. Thus, the plug segments guarantee the desired alignment of transmitter and receiver elements 6 and 5. On each plug segment 17 or 18, a flange segment 19 and/or 20 is mounted, preferably of one integral piece therewith. Each flange segment forms a stop during the plugging in or insertion to prevent the plug segments from sinking all the way into the foam material part. The flange shape can be adapted to the exterior contour of foam part 1, in other words it can be curved. Transmitter element 6 is connected with receiver element 5 through a connecting line 21. Connection 22 connects receiver element 5 and/or transmitter element 6 with a reading and/or analysis device.

Figure 3:
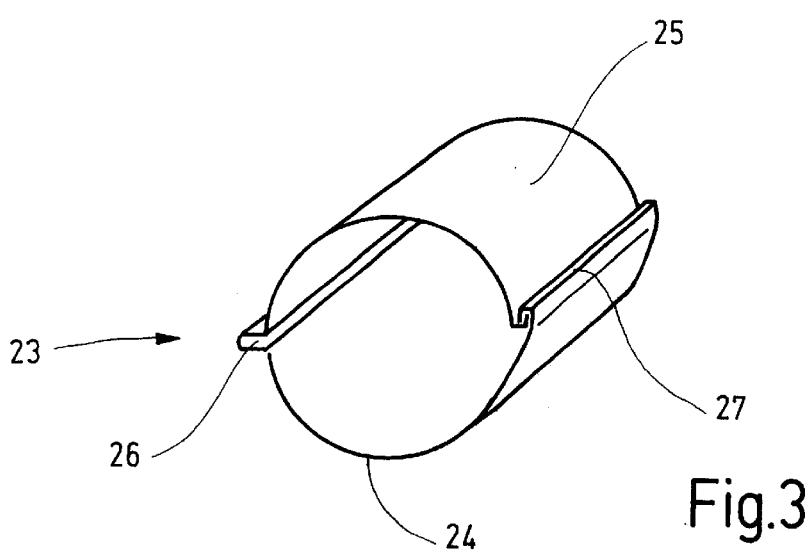
FIG. 3 is a perspective view of a plastic or metal sheathing according to a second embodiment of the present invention.

FIG. 3 shows a sheathing 23 of either plastic or metal, forming a rigid casing around the carrier means and around foam material part 1. Sheathing 23 includes two half-shells 24, 25 each of which is essentially semi-cylindrical in cross section. The half-shells are connected with one another by articulation on their edges facing one another by a hinge 26 and have a hook- or catch-like closing 27 along the respective facing side edges. Half-shells 24, 25 are preferably formed of a rigid, thin plastic or metal and are elastically deformable, particularly in radial direction, for the closing or opening. Alternatively or supplemental thereto, other closing mechanisms, for example catch closings, adhering closings or adhesive closings can be inserted into hook- or catch-like closing 27. In the example shown, the complete carrier or carrier means is formed by the combination of foam material part 1 with the sheathing 23.

Figure 4:
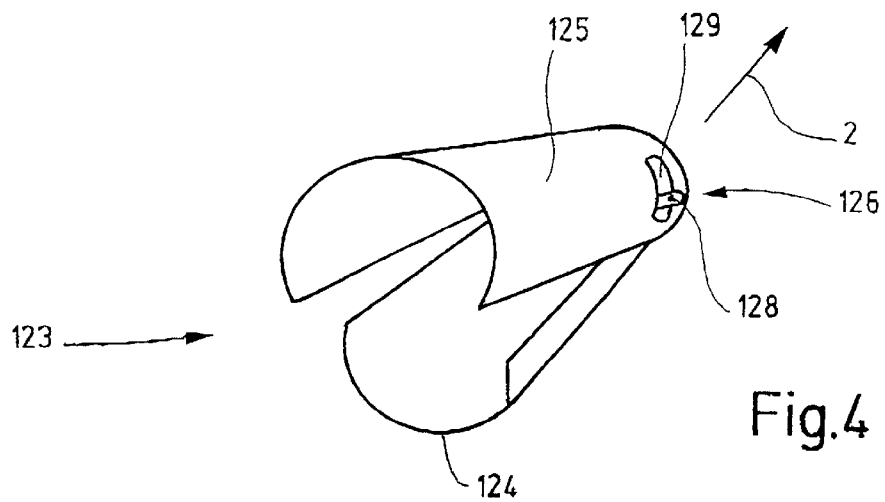
FIG. 4 is a perspective view of a two-part sheathing tapering conically according to a third embodiment of the present invention.

FIG. 4 shows a similar two-part sheathing 123 conically tapering in longitudinal direction 2. This sheathing tapers in the direction toward the axial end hinge 126 allowing for folding back of one part for the insertion of a foam material part. The foam material can optionally also be conical. Hinge 126 is formed by axle journals 128 configured of one piece with the first half-shell 124. The axle journals engage in corresponding openings 129 of the second half-shell 125. First half-shell 124 is essentially semi-circular in cross section. Second half-shell 125 in cross section forms a circle segment of more than 180 degrees. Upon folding together, the first half-shell 124 connects by snapping into second half-shell 125. The cohesion in the snapped-together state is adjustable by the design of half-shells 124, 125, particularly by relative spreading of first half-shell 124 and/or by crimping of second half-shell 125.

Figure 5:
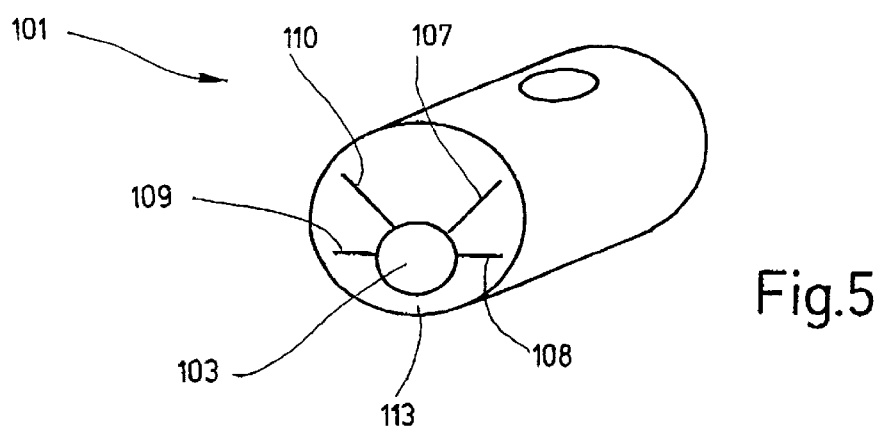
FIG. 5 is a perspective view of a foam material part of a carrier according to a fourth embodiment of the present invention.

FIG. 5 shows an alternative embodiment of foam material part 101, in which longitudinal opening 103 extends eccentrically relative to the middle axis of foam material part 101. Incisions 107, 108, 109, 110 are not uniformly distributed around the opening periphery, but rather form one segment 113 much closer to the side of longitudinal opening 103 associated with the receiver element 6. Segment 113 extends, for example, over approximately a breadth of 180 degrees and has only a short radial extension. By the eccentric arrangement of longitudinal opening 103, it is guaranteed that one of the measuring means, particularly receiver element 5, engages directly on the body part or in any case is arranged to be directly thereon.

As a result of the design selection, and if necessary, the changing of the diameter of sheathing 23, 123 either over its entire axial extension, or over a part of it or even only at certain points on segments thereof, a prebiasing or initial stress of foam material part 1, 101 can be attained in predeterminable measure. The shape of sheathing 23 or 123 can likewise be identical to the exterior shape of foam part 1, 101, 201 and/or the shape of longitudinal opening 3 or 103. In other words, it can be cylindrical, conical, bulging or corrugated, and in particular, can be adapted to the shape of the body part receiving it. When sheathing 23 or 123 is of a shorter axial extension than foam part 1 or 101, the body part is protected from injury or lesions caused at the borders of the axial ends of sheathing 23 or 123 by the projecting foam material part 1 or 101. Foam part 1, 101 or 201 and/or sheathing 23 or 123 can include a stop fixture for the introduction of the body part or during the slipping over of the device. Sheathing 23 or 123 can have bulging blocking parts projecting radially inward, which prevent deformation and particularly prevent sliding of foam material part 1 or 101 in longitudinal direction 2.

Figure 6:
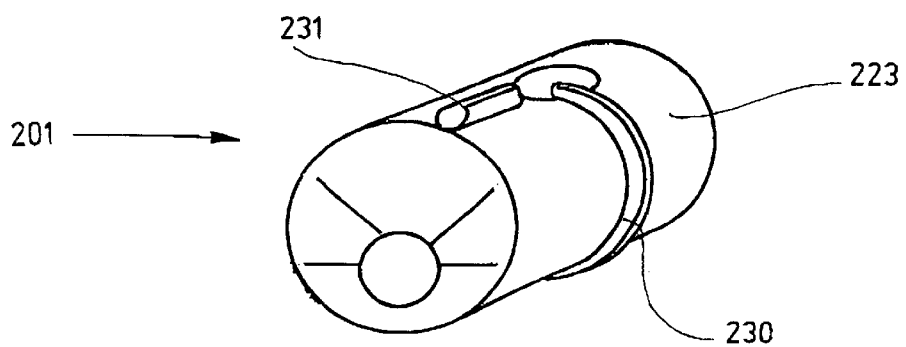
FIG. 6 is a perspective view of a carrier according to a fifth embodiment of the present invention.

FIG. 6 shows an exemplary embodiment of the carrier or carrier means, in which foam material part 201 is made up of one integral piece with casing or sheathing 223, for example, with use of integral or structural foam parts having a solid skin and a cellular core. Clamping means in the form of slotted tubes 230 and 231 are preferably formed of one integral piece with sheathing 223 on the exterior. A first slotted tube 230 receives connecting line 21 between transmitter element 6 and receiver element 5, and extends essentially around half of the peripheral surface. A second, particularly a straight slotted tube 231 extends along the exterior of sheathing 223 and receives the connection 22. Slotted tubes 230 and 231 are elastic so that they can be spread open. Allowing the connecting line 21 and connection 22 to be simply and detachably mounted on foam material part 201.

While various embodiments have been chosen to illustrate the invention, it will be understood by those skilled in the art that various changes and modifications can be made therein without departing from the scope of the invention as defined in the appended claims.

What is claimed is:

1. An arrangement for attaching a medical-technical sensor to a patient's body part, comprising:
   a carrier including an elastically deformable foam material part having a longitudinal direction, said foam material part being preformed as at least a partial tubular body;
   a longitudinal opening in said foam material part extending in the longitudinal direction for receiving the body part;
   slits extending in said foam material part radially relative to said longitudinal opening; and
   a sensor support on said carrier.
2. An arrangement according to claim 1 wherein said foam material part is a cylinder.
3. An arrangement according to claim 2 wherein said cylinder is a right circular cylinder.
4. An arrangement according to claim 1 wherein said foam material part is at least partially conical and tapers in the longitudinal direction.
5. An arrangement according to claim 1 wherein said slits originate at said longitudinal opening and extend in the longitudinal direction to define at least two arcuate segments.
6. An arrangement according to claim 5 wherein said slits extend radially through at least one-half of a thickness of said foam material part.
7. An arrangement according to claim 5 wherein said segments are unitarily connected with one another by a peripheral portion of said foam material part.
8. An arrangement according to claim 1 wherein said foam material part has a continuous, homogeneous, uninterrupted peripheral portion.
9. An arrangement according to claim 1 wherein said longitudinal opening has a shape corresponding to the body part to be received therein.
10. An arrangement according to claim 1 wherein said foam material part comprises a transverse opening forming said sensor support.
11. An arrangement according to claim 1 wherein said carrier comprises an exterior with at least one part mounting a connection coupled to the sensor.
12. An arrangement according to claim 1 wherein said foam material part is surrounded by a rigid sheathing.
13. An arrangement according to claim 12 wherein said sheathing is formed of metal.
14. An arrangement according to claim 12 wherein said sheathing is formed of plastic.
15. An arrangement according to claim 12 wherein said sheathing is formed of separable parts that can be opened to receive said foam material part.
16. An arrangement according to claim 1 wherein said foam material part is colored with a dye corresponding to an optical electronic measurement performed by the sensor.
17. A medical-technical sensor attachable to a patient's body part, comprising:
   a carrier including an elastically deformable foam material part having a longitudinal direction, said foam material part being preformed as at least a partial tubular body;
   a longitudinal opening in said foam material part extending in the longitudinal direction for receiving the body part;
   slits extending in said foam material part radially relative to said longitudinal opening; and
   a sensor supported by said carrier.
18. A medical-technical sensor according to claim 17 wherein
   said sensor comprises at least one optical transmitter and at least one optical receiver arranged on opposite sides of said carrier.
19. A medical-technical sensor according to claim 17 wherein
   said foam material part is essentially impermeable to radiation of said sensor.
20. A medical-medical sensor according to claim 19 wherein
   said foam material part is impermeable to said radiation by a correspondingly suitable color.

* * * * *